United States Patent [19]
Engelbrecht et al.

[11] Patent Number: 5,782,923
[45] Date of Patent: Jul. 21, 1998

[54] ENDOPROSTHESIS FOR AN ELBOW JOINT

[75] Inventors: Eckart Engelbrecht, Hamburg; Arnold Keller, Kayhude, both of Germany

[73] Assignees: GMT Gesellschaft Fuer Medizinische Technik mbH; Waldemar Link GmbH & Co. KG, both of Hamburg, Germany

[21] Appl. No.: 859,734

[22] Filed: May 21, 1997

[30] Foreign Application Priority Data

May 22, 1996 [DE] Germany ............ 196 20 525.5

[51] Int. Cl.⁶ .................................................. A61F 2/38
[52] U.S. Cl. ................................................... 623/20
[58] Field of Search ................................ 623/20, 21

[56] References Cited

U.S. PATENT DOCUMENTS

| | | | |
|---|---|---|---|
| 4,129,902 | 12/1978 | Harmon | 623/20 |
| 4,224,695 | 9/1980 | Grundei | 623/20 |
| 4,259,752 | 4/1981 | Taleisnik | 623/21 |
| 4,307,473 | 12/1981 | Weber | 623/21 |
| 5,133,762 | 7/1992 | Branemark | 623/21 |
| 5,458,644 | 10/1995 | Grundei | 623/20 |

*Primary Examiner*—Michael J. Milano
*Attorney, Agent, or Firm*—Henry M. Feiereisen

[57] ABSTRACT

An endoprosthesis for an elbow joint, includes a humeral component having a shaft portion adapted for engagement in the bone canal of a humerus, an ulnar component having a shaft portion adapted for engagement in the bone canal of a ulnar, and a radius component having a shaft portion adapted for engagement in the bone canal of a radius, with the ulnar component being supported by a swivel bearing in an area of the humeral component. A lateral flange projects outwardly form the ulnar component and is formed with a socket for guiding a sliding member for displacement therein, with the radius component having a head portion which is swingably mounted in the sliding member.

31 Claims, 3 Drawing Sheets

FIG. 1
FIG. 2
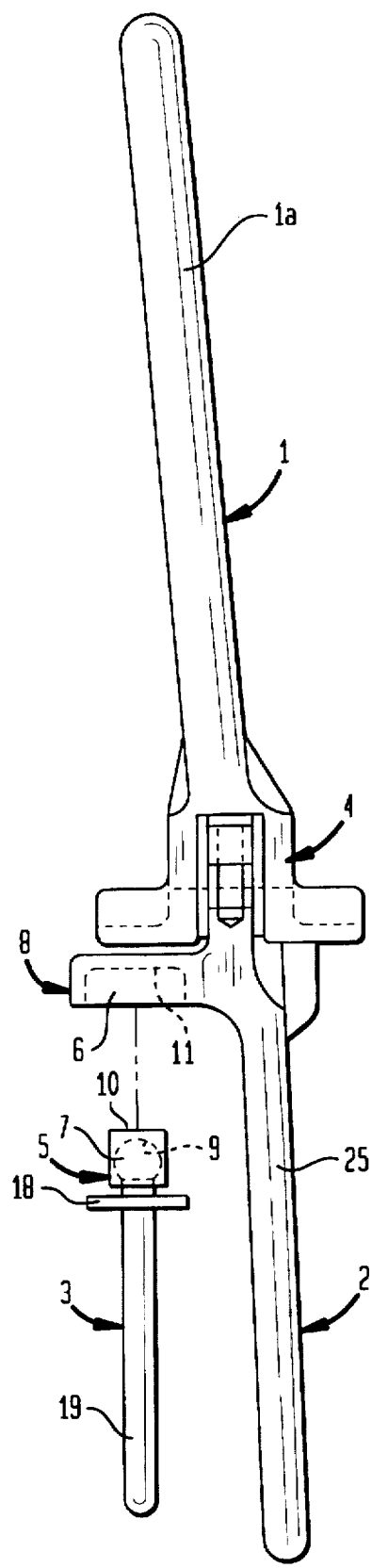
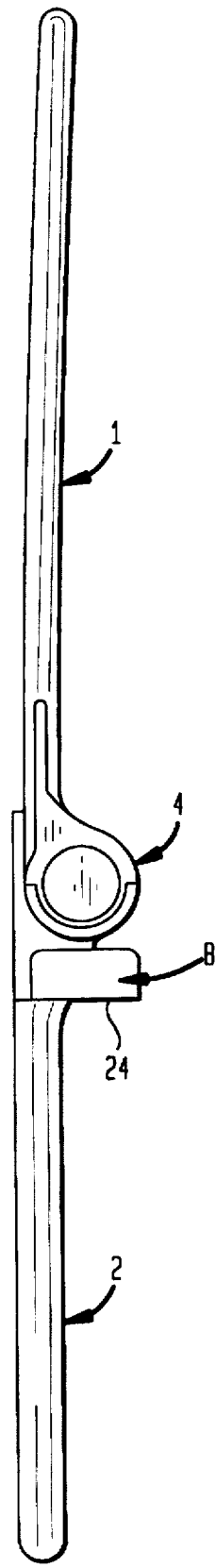

ENDOPROSTHESIS FOR AN ELBOW JOINT

BACKGROUND OF THE INVENTION

The present invention refers to an endoprosthesis for an elbow joint, and in particular to an endoprosthesis of a type having a humeral component including a shaft portion adapted for engagement in the bone canal of a humerus, an ulnar component including a shaft portion adapted for engagement in the bone canal of an ulnar, and a radius component including a shaft portion adapted for engagement in the bone canal of a radius, with the ulnar component being supported by a swivel bearing in an area of the humeral component.

German publication DE-OS 3940728 discloses an endoprosthesis for an elbow joint of this type, with the radius component having a head portion which is swingably supported at lateral clearance directly in a socket provided on the underside of a flange or lateral extension that projects from the ulnar component. In this manner, the radius component can swing together with the ulnar component about the swivel axis of the swivel bearing when the forearm is bent or stretched, and is capable to so move relative to the ulnar component, e.g. during a rotation of the forearm about its longitudinal axis, as to prevent the radius component from being subject to a torsional load or bending load that could lead to a loosening of its shaft portion.

Although this type of construction seems to be sound because of its ability to realize various motions that substantially simulate conditions in a natural elbow joint. Tests have shown however that the mobility of the radius component relative to the ulnar component could be further optimized, especially with regard to an improved execution of the swivel motions of the radius head, without adversely affecting the transversal mobility of the radius head within the socket.

SUMMARY OF THE INVENTION

It is thus an object of the present invention to provide an improved endoprosthesis for an elbow joint, which has an improved articulation between the radius component and the ulnar component.

This object, and others which will become apparent hereinafter, are attained in accordance with the present invention by providing a support unit for connecting the radius component to the ulnar component for articulation, wherein the support unit includes a socket, and a sliding member guided in the socket for displacement therein, with the radius component being swingably mounted in the sliding member.

In contrast to the conventional radius head which is so received in the socket as to be freely movable therein and also swingable as well as displaceable therein, the connection between the radius component and the ulnar component in accordance with the present invention is effected by two separate articulation surfaces, i.e. a partially spherical sliding surface for swivel movements between the radius head and the sliding member, and a substantially flat sliding surface for transverse mobility between the sliding member and the socket. Thus, an improved execution of swivel movements is attained between the radius head and the ulnar component, without relinquishing the transverse mobility of the radius head within the socket. Moreover, compared to a radius head that freely floats in the socket, the sliding member can be better secured in the socket by muscles and ligaments so that the risk of luxation in the area of support of the radius head is reduced when being subject to extreme strain. The enlargement of the articulation surfaces as attained by the innovative articulation between the radius component and the ulnar component also reduces the contact pressure between surfaces that slide upon one another and minimizes a wear of prosthesis parts that are made of softer plastic material.

According to another feature of the present invention, the sliding member is movable along two degrees of freedom in a direction perpendicular to a central socket axis so as to be shiftable within the socket in the direction of the shaft portion of the ulnar component as well as in the direction transversely thereto. Suitably, the sliding member exhibits a flat top which bears upon a correspondingly flat bottom of the socket and has lateral dimensions which are smaller than the corresponding inner dimensions of the socket so that a clearance of at least 1 mm or preferably slightly more is effected all-around between a circumferential inner socket wall, which bounds the bottom, and a lateral circumferential surface of the sliding member when the sliding member occupies in its quiescent position a central disposition in the socket and the forearm is not rotated. Preferably, the sliding member and the inner socket wall have a rotationally symmetric configuration with respect to their center axes which suitably coincide when the sliding member is received centrally in the socket. However, it is certainly possible to select asymmetric configurations as well, in particular as far as the inner socket wall is concerned, which e.g. may be configured in the form of an ellipse. In any event, it is important to so configure the inner socket wall that the sliding member is guided along the inner socket wall without any risk of becoming jammed in the socket. Suitably, the inner socket wall is formed with sections that continuously blend into one another, with each section exhibiting a flat contact surface for the sliding member.

The association of the sliding member relative to the socket suitably depends on respective anatomic conditions of a patient being supplied with the prosthesis and on a respective tilting position of the radius component. These factors also decide the disposition of the sliding member relative to the socket when the sliding member occupies its quiescent position and the forearm is not rotated. In this quiescent position, the sliding member can also be positioned out-of-center within the socket.

According to still another feature of the present invention, the sliding member is formed with a partially spherical recess that complements the ball-shaped configuration of the radius head and is engaged substantially free of clearance by the radius head so that the outer surface of the radius head and the inner surface of the recess bear and slide upon one another, thereby defining the articulation surface for the swivel motion of the radius head relative to the ulnar component. Preferably, the partially spherical inner surface of the recess slightly exceeds the surface of a hemisphere. As a consequence, the radius head is retained within the sliding member and an axial movement between the sliding member and the radius head is eliminated.

Suitably, the sliding member is formed with an opening for passage of the radius head and is made of plastic material which is compatible to a wearer's body, preferably of high density polyethylene (HDPE). This material exhibits a sufficient elasticity to enable a captivation of the radius head in the recess as the wall surrounding the opening can be elastically widened during insertion of the radius head until the radius head snaps into the recess. As a result of the elastic restoring force, the deformed wall area returns to its initial position.

The socket is preferably formed at the underside thereof with a flange which projects substantially perpendicular to the shaft portion of the ulnar component and to the swivel plane of the swivel bearing, whereby the flange is suitably connected in one piece with the ulnar component so that the flange and thus the socket can pivot together with the ulnar component relative to the humeral component. Like the humeral component and the radius component with its head portion, the ulnar component and the flange are preferably made from a metallic implant material which is compatible to a wearer's body, preferably of a CoCrMo alloy so that in conjunction with the sliding member that is made of high density polyethylene a wear-reducing material combination of CoCrMo/HDPE is effected in the area of the flat articulation surface between the sliding member and the bottom of the socket as well as in the area of the partially spherical articulation surface between the radius head and the sliding member.

BRIEF DESCRIPTION OF THE DRAWING

The above and other objects, features and advantages of the present invention will now be described in more detail with reference to the accompanying drawing in which:

FIG. 1 is a schematic, partially exploded, front view of an endoprosthesis for an elbow joint in accordance with the present invention;

FIG. 2 is a side view of the endoprosthesis, illustrating in detail a humeral component and an ulnar component thereof;

DETAILED DESCRIPTION OF PREFERRED EMBODIMENTS

Figure 3:
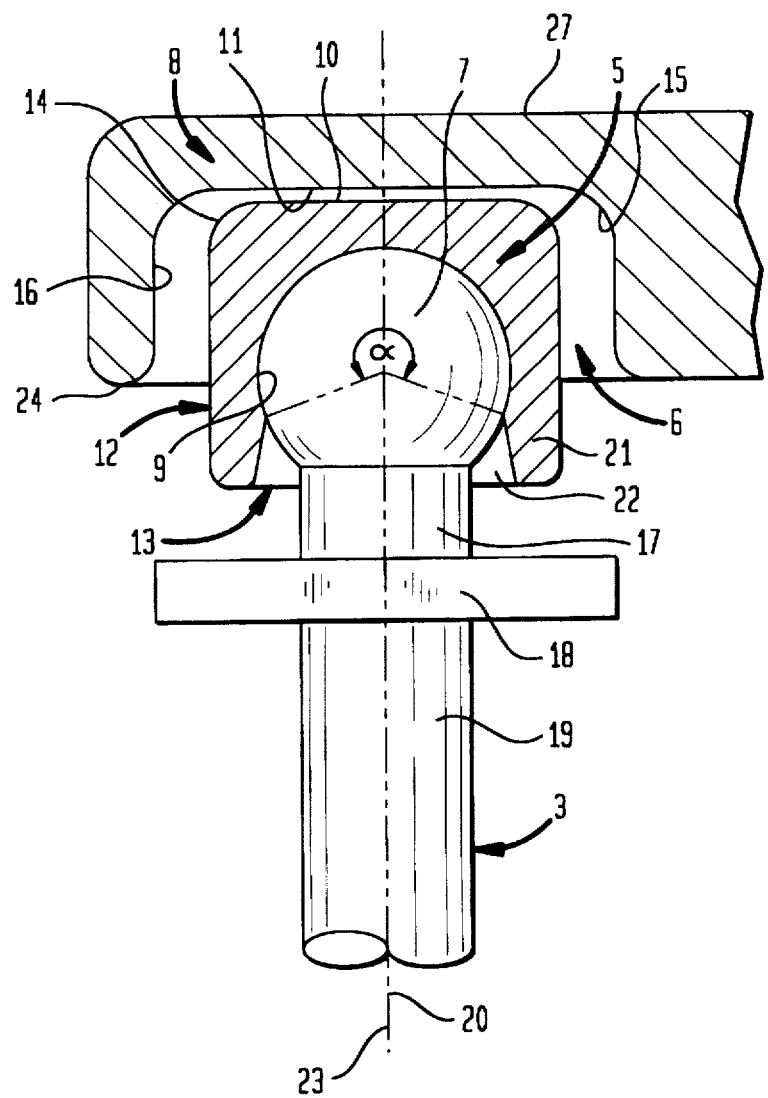
FIG. 3 is a cutaway, longitudinal section of the endoprosthesis, showing in detail a sliding member received in the socket of the ulnar component and a radius head locked in place within the sliding member.

Throughout all the Figures, the same or corresponding elements are generally indicated by the same reference numerals.

Turning now to the drawing, and in particular to FIG. 1, there is shown a schematic, partially exploded front view of an endoprosthesis for an elbow joint, in accordance with the present invention, substantially including a humeral component 1 which includes a shaft portion 1a adapted to be received in the bone canal of the humerus, and an ulnar component 2 including a shaft portion 25 adapted to be received in the bone canal of the ulnar and swingably supported by the humeral component 1 via a swivel bearing, generally designated by reference numeral 4, and a radius component 3 including a shaft portion 19 adapted to be received in the bone canal of the radius. The radius component 3 has a spherical head portion 7 (FIG. 3) which is inserted in a spherical recess 9 of a sliding member 5. Projecting outwardly from the ulnar shaft portion 25 is a flange, generally designated by reference numeral 8. The flange 8 has an underside which is formed with a socket 6 for so receiving the sliding member 5 as to allow a displacement of the sliding member 5 in a transverse direction.

As shown in FIG. 2, the swivel bearing 4 for swingably supporting the ulnar component 2 relative to the humeral component 1 is of conventional design, as described e.g. in the commonly owned German publication DE-OS 39 40 728, the disclosure of which is incorporated herein by reference. Therefore, a detailed description of the swivel bearing 4 and the humeral component 1 is omitted for the sake of simplicity.

The sliding member 5 is made of plastic material that is compatible to a wearer's body, preferably of high density polyethylene (HDPE). As shown in FIG. 3, the sliding member 5 is formed by a substantially flat top 10, which bears against a downwardly directed, flat bottom 11 of the socket 6, a cylindrical circumferential surface 12 which extends perpendicular to the top 10, and a bottom 13 which faces the radius component 3. The recess 9 of the sliding member 5 for receiving the radius head 7 terminates in the bottom 13. The circumferential surface 12 and the top 10 are connected to one another via a circumferential edge 14 of rounded configuration, with the radius of curvature of the edge 14 corresponding to the radius of curvature of a rounded transition 15 between the bottom 11 of the socket 6 and an inner socket wall 16 which laterally bounds the bottom 11.

The diameter of the recess 9 corresponds to the diameter of the radius head 7 so that the partially spherical inner area of the recess 9 bears against the spherical surface of the radius head 7 to slide thereupon. The radius head 7 is connected to the shaft portion 19 via a slender cylindrical neck 17 and a subjacent disk-shaped collar 18 of circular cross section, with the shaft portion 19 and the neck 17 having a same diameter. The radius component 3 is preferably made in one piece of CoCrMo alloy so that the articulation surfaces for the swivel motion, i.e. the partially spherical inner surface of the recess 9 and the spherical surface of the head portion 7, which bear and glide on one another, are formed by a wear-resistant material combination of HDPE/CoCrMo.

The inner partially spherical surface of the recess 9 slightly exceeds the surface of the hemisphere, i.e. the center angle a defined in a section plane through the center axis 20 of the radius component 3 exceeds 180° so that a major portion of the circumference of the radius head 7, when being inserted in the recess 9, is surrounded in the section plane by the sliding member 5 and thereby securely retained within the recess 9. The insertion of the radius head 7 in the recess 9 is effected by elastically widening the wall 21 of the sliding member 5 in the area of its opening 22 to such a degree that the radius head 7 snaps into the recess 9, i.e. passes with its greatest diameter through the opening 22. In order to facilitate the insertion of the radius head 7 into the recess 9, the opening 22 is tapered towards the inside so that the wall 21 widens in this area as a result of wedge forces when the upper area of the radius head 7 is inserted from outside through the opening 22, and the radius component 3 is acted upon by an axial pressure force. After captivation of the radius head 7, the deformed wall 21 of the sliding member 5 returns to its original configuration as a consequence of the elastic restoring force and securely holds the radius head 7 in the recess 9.

The cylindrical inner wall 16 of the socket 6 is rotationally symmetrical with respect to its center axis 23 and has a diameter which is slightly greater than the outer diameter of the cylindrical circumferential surface 12 of the sliding member 5 so that a central disposition of the radius head 7 in the socket 6 and coinciding center axes 20,23, in correspondence to an quiescent position of the radius component 3 when the forearm is not rotated, result in a greater clearance for laxity in an area between the inner socket wall 16 and the circumferential surface 12 of the sliding member 5. For example, when the socket 6 has an inner diameter of 13 mm, the outer diameter of the circumferential surface 12 may measure 10 mm so that the created clearance for laxity, i.e. the width of a circumferential gap between the sliding member 5 and the socket 6, amounts in the quiescent position to 1.5 mm. As a consequence of the clearance, the sliding member 5 can be displaced parallel to the bottom 11 of the socket 6 with two degrees of freedom when the forearm is rotated about its longitudinal axis, with the sliding member 5 adjusting in the socket 6 in correspondence to anatomic conditions and the tilting position of the radius component 3. When implanting the endoprosthesis for the elbow joint, the sliding member 5 seeks in its quiescent position at non-rotated forearm a central disposition with respect to the socket 6. The socket 6 may however exhibit also a configuration that differs from the rotational symmetry, e.g. the socket 6 may display an elliptic boundary. Important is only that the sliding member 5 can bear upon the inner socket wall 16 without becoming jammed in the socket 6.

The ratio between the depth of the downwardly open socket 6 and the height of the sliding member 5 is in the range between approximately 1:2 and 2:3 so that the sliding member 5 projects partially downwards beyond a flat lower edge 24 (FIG. 2) of the socket 6. At a height of the sliding member 5 of about 9 mm, the depth of the socket 6 may measure about 5–7 mm and is thus of sufficient size to retain the sliding member 5 together with the muscles and ligaments, guided along the neck 17, within the socket 6.

The flange 8 with its socket 6 is formed at the upper end of the ulnar component 2 and extends substantially perpendicular to the shaft portion 25 of the ulnar component 2 and to the swivel plane of the swivel bearing 4, with the flange 8 projecting laterally beyond the ulnar component 2 in direction toward the outside of the elbow joint. The flange 8 is formed with a flat top 27 with rounded edges which terminate in respective three boundary sides that extend substantially perpendicular to the top 27.

The ulnar component 2 and the attached flange 8 are made of a CoCrMo alloy so that a wear-resistant material combination of CoCrMo/HDPE is provided at the articulation surface for the transverse displacement, formed by areas of the socket 6 and the sliding member 5 that slide upon one another, i.e. by the flat socket bottom 11 and the top 10 of the sliding member 5.

Figure 4:
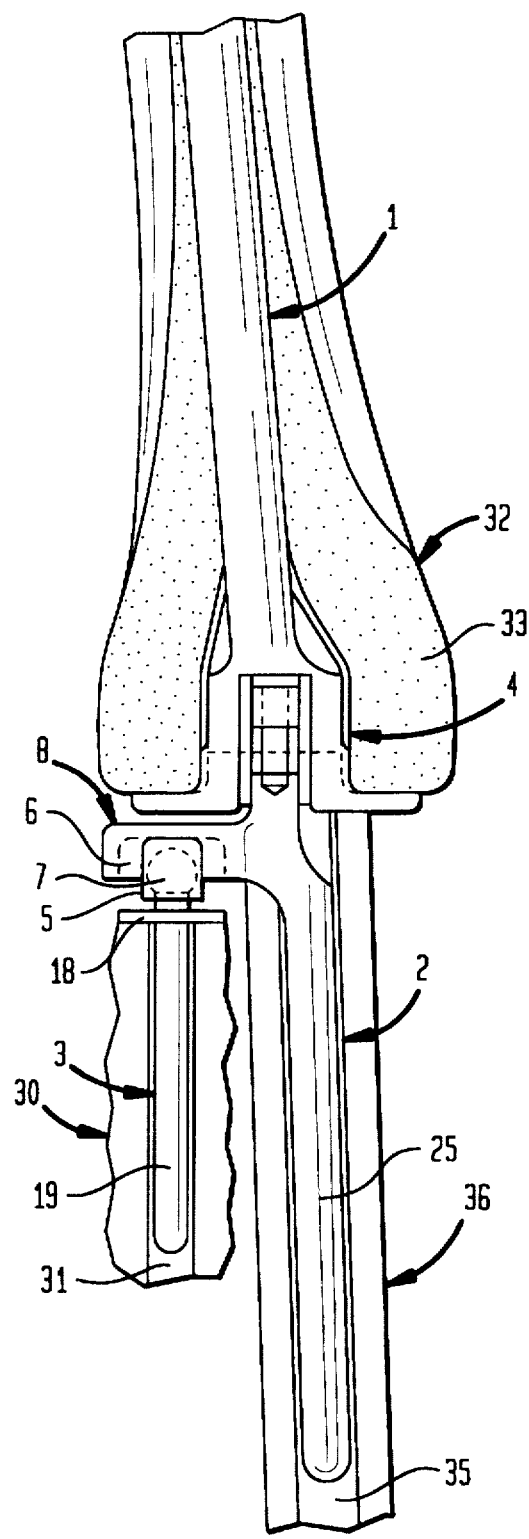
FIG. 4 is a simplified, partially sectional front view of the endoprosthesis, implanted in a human elbow joint.

Turning now to FIG. 4, there is shown a simplified, partially sectional front view of the endoprosthesis, implanted in a human elbow joint. As can be seen from FIG. 4, the collar 18 of the radius component 3 bears with its underside upon a resected portion at the upper end of the separated radius 30 while the shaft portion 19 is anchored in the bone canal 31 of the radius 30. The resected portion of the radius 30 is so arranged that the distance thereof to the bottom 11 of the socket 6 equals the distance between the underside of the collar 18 and the top 10 of the sliding member 5 that is in engagement with the radius head 7. The humeral component 1 is inserted with its shaft portion 1a in the bone canal of the humerus 32. The lower end of the humerus 32 is formed by the spongiosa bone 33 which has previously been milled out to receive the swivel bearing 4 while the shaft portion 25 of the ulnar component 2 is anchored in the bone canal 35 of the ulna 36.

While the invention has been illustrated and described as embodied in an endoprosthesis for an elbow joint, it is not intended to be limited to the details shown since various modifications and structural changes may be made without departing in any way from the spirit of the present invention.

What is claimed as new and desired to be protected by letters patent is set forth in the appended claims:

What is claimed is:

1. An endoprosthesis for an elbow joint, comprising:
   a humeral component adapted for engagement in a bone canal of a humerus;
   an ulnar component adapted for engagement in a bone canal of an ulnar;
   a radius component adapted for engagement in a bone canal of a radius;
   a swivel bearing for supporting the ulnar component in an area of the humeral component; and
   support means connecting the radius component to the ulnar component for articulation, said support means including a socket, and a sliding member guided in the socket for displacement therein, said radius component being swingably mounted in the sliding member.

2. The endoprosthesis of claim 1 wherein the socket is defined by a center axis, said sliding member being guided in the socket for displacement in two degrees of freedom perpendicular to the center axis.

3. The endoprosthesis of claim 1 wherein the sliding member is randomly positionable at each point of the socket in dependence on anatomic conditions and a tilted position of the radius component.

4. The endoprosthesis of claim 1 wherein the sliding member is received in a central disposition in the socket when the forearm is not rotated.

5. The endoprosthesis of claim 1 wherein the sliding member is rotationally symmetric to a center axis thereof.

6. The endoprosthesis of claim 1 wherein the sliding member has a width which is smaller than inner dimensions of the socket.

7. The endoprosthesis of claim 1 wherein the socket has a downwardly directed bottom, said sliding member sliding upon the bottom.

8. The endoprosthesis of claim 7 wherein the sliding member has a top facing the bottom of the socket, said top and said bottom exhibiting a substantially flat configuration.

9. The endoprosthesis of claim 1 wherein the socket is defined by a depth and the sliding member is defined by a height which at least corresponds to the depth of the socket.

10. The endoprosthesis of claim 1 wherein the socket has a circumferential inner wall for providing a lateral stop for the sliding member.

11. The endoprosthesis of claim 10 wherein the inner wall has sections which continuously blend into one another to effect a flat contact surface for the sliding member.

12. The endoprosthesis of claim 10 wherein the inner wall is configured in the form of an ellipse.

13. The endoprosthesis of claim 10 wherein the inner wall is rotationally symmetric with respect to a center axis of the socket.

14. The endoprosthesis of claim 10 wherein the socket exhibits a downwardly directed bottom which is connected to the inner wall of the socket via a rounded transition.

15. The endoprosthesis of claim 10 wherein the sliding member has a top and a lateral circumferential surface facing the inner wall of the socket, said top and said lateral circumferential surface being connected by a rounded transition.

16. The endoprosthesis of claim 1 wherein the radius component has a rounded head portion which is partially circumscribed by the sliding member.

17. The endoprosthesis of claim 16 wherein the sliding member is formed with a recess complementing a configuration of the head portion of the radius component.

18. The endoprosthesis of claim 17 wherein the head portion and the recess have complementing spherical surfaces.

19. The endoprosthesis of claim 18 wherein the spherical surface of the recess slightly exceeds a surface of a hemisphere.

20. The endoprosthesis of claim 16 wherein the head portion of the radius component snaps in the sliding member.

21. The endoprosthesis of claim 1 wherein the sliding member is made of a plastic material that is compatible with a wearer's body.

22. The endoprosthesis of claim 1 wherein the sliding member is made of high density polyethylene (HDPE).

23. The endoprosthesis of claim 1 wherein the ulnar component has a shaft portion for insertion in the bone canal of the ulnar, said support means including a lateral flange projecting from the ulnar component and having an underside so configured as to form the socket, said flange projecting substantially perpendicular to the shaft portion of the ulnar component and to a swivel plane of the swivel bearing so as to jut laterally beyond the ulnar component.

24. The endoprosthesis of claim 23 wherein the flange is formed in one piece with the ulnar component.

25. The endoprosthesis of claim 23 wherein the ulnar component and the flange are made of a metal which is compatible with a wearer's body.

26. The endoprosthesis of claim 23 wherein the ulnar component and the flange are made of a CoCrMo alloy.

27. The endoprosthesis of claim 1 wherein the radius component is formed in one piece and made of a metal which is compatible with a wearer's body.

28. The endoprosthesis of claim 23 wherein the radius component is made of a CoCrMo alloy.

29. The endoprosthesis of claim 16 wherein the radius component has a cylindrical neck adjacent the head portion of the radius component.

30. The endoprosthesis of claim 29 wherein the radius component has a shaft portion for insertion in the bone canal of the radius, and a collar positioned between the neck and the shaft portion of the radius component.

31. The endoprosthesis of claim 30 wherein the radius component is rotationally symmetrical to a center axis of the shaft portion of the radius component.

* * * * *